US011904185B2

(12) United States Patent
Hirayama et al.

(10) Patent No.: US 11,904,185 B2
(45) Date of Patent: Feb. 20, 2024

(54) PARTICLE THERAPY SYSTEM, DOSE DISTRIBUTION EVALUATION SYSTEM, AND METHOD FOR OPERATING PARTICLE THERAPY SYSTEM

(71) Applicants: HITACHI, LTD., Tokyo (JP); NATIONAL UNIVERSITY CORPORATION HOKKAIDO UNIVERSITY, Hokkaido (JP)

(72) Inventors: Shusuke Hirayama, Sapporo (JP); Rintarou Fujimoto, Tokyo (JP); Masumi Umezawa, Tokyo (JP); Yuusuke Fujii, Tokyo (JP); Keiji Kobashi, Sapporo (JP); Taeko Matsuura, Sapporo (JP); Shinichi Shimizu, Sapporo (JP)

(73) Assignees: HITACHI, LTD., Tokyo (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 14 days.

(21) Appl. No.: 17/289,346

(22) PCT Filed: Nov. 15, 2019

(86) PCT No.: PCT/JP2019/044837
§ 371 (c)(1),
(2) Date: Apr. 28, 2021

(87) PCT Pub. No.: WO2020/137234
PCT Pub. Date: Jul. 2, 2020

(65) Prior Publication Data
US 2021/0393985 A1 Dec. 23, 2021

(30) Foreign Application Priority Data
Dec. 25, 2018 (JP) ................................ 2018-240752

(51) Int. Cl.
*A61N 5/10* (2006.01)
*G01T 1/02* (2006.01)

(52) U.S. Cl.
CPC .............. *A61N 5/1071* (2013.01); *G01T 1/02* (2013.01); *A61N 2005/1087* (2013.01)

(58) Field of Classification Search
CPC .......... A61N 5/1071; A61N 2005/1087; A61N 2005/1061; A61N 5/1049; A61N 5/1067; G01T 1/02
See application file for complete search history.

(56) References Cited

U.S. PATENT DOCUMENTS

2012/0161030 A1 6/2012 Iwata et al.
2020/0054897 A1 2/2020 Fujii et al.

FOREIGN PATENT DOCUMENTS

JP       5496364 B2     5/2014
JP    2014-132935 A    7/2014
(Continued)

OTHER PUBLICATIONS

International Search Report of PCT/JP2019/044837 dated Jan. 7, 2020.

*Primary Examiner* — Marcus H Taningco
(74) *Attorney, Agent, or Firm* — Mattingly & Malur, PC

(57) ABSTRACT

A proton beam therapy system 1 includes an irradiation nozzle 25 for irradiating a target 31A with a particle beam, a proton beam irradiation control system 41 that controls the irradiation nozzle 25, a dose monitor 27B that measures an irradiation amount of the particle beam emitted to the target 31A, a position monitor 27A that measures a position of the particle beam emitted to the target 31A, and a dose distribution evaluation system during irradiation 55 that calculates a dose distribution of the particle beam emitted to the target 31A during irradiation. This system supports a medical staff to quickly and appropriately make an intervention (Continued)

determination for treatment such as discontinuation of particle therapy, a change in conditions thereof, or the like in the process of particle irradiation.

13 Claims, 9 Drawing Sheets

(56) References Cited

FOREIGN PATENT DOCUMENTS

| | | | | |
|---|---|---|---|---|
| JP | 2015500053 A | * | 1/2015 | ............... A61N 5/10 |
| JP | 2017-176533 A | | 2/2020 | |
| WO | WO-2017170178 A1 | * | 10/2017 | ............. A61B 6/032 |
| WO | 2017/199390 A | | 11/2017 | |

* cited by examiner

[FIG. 1]
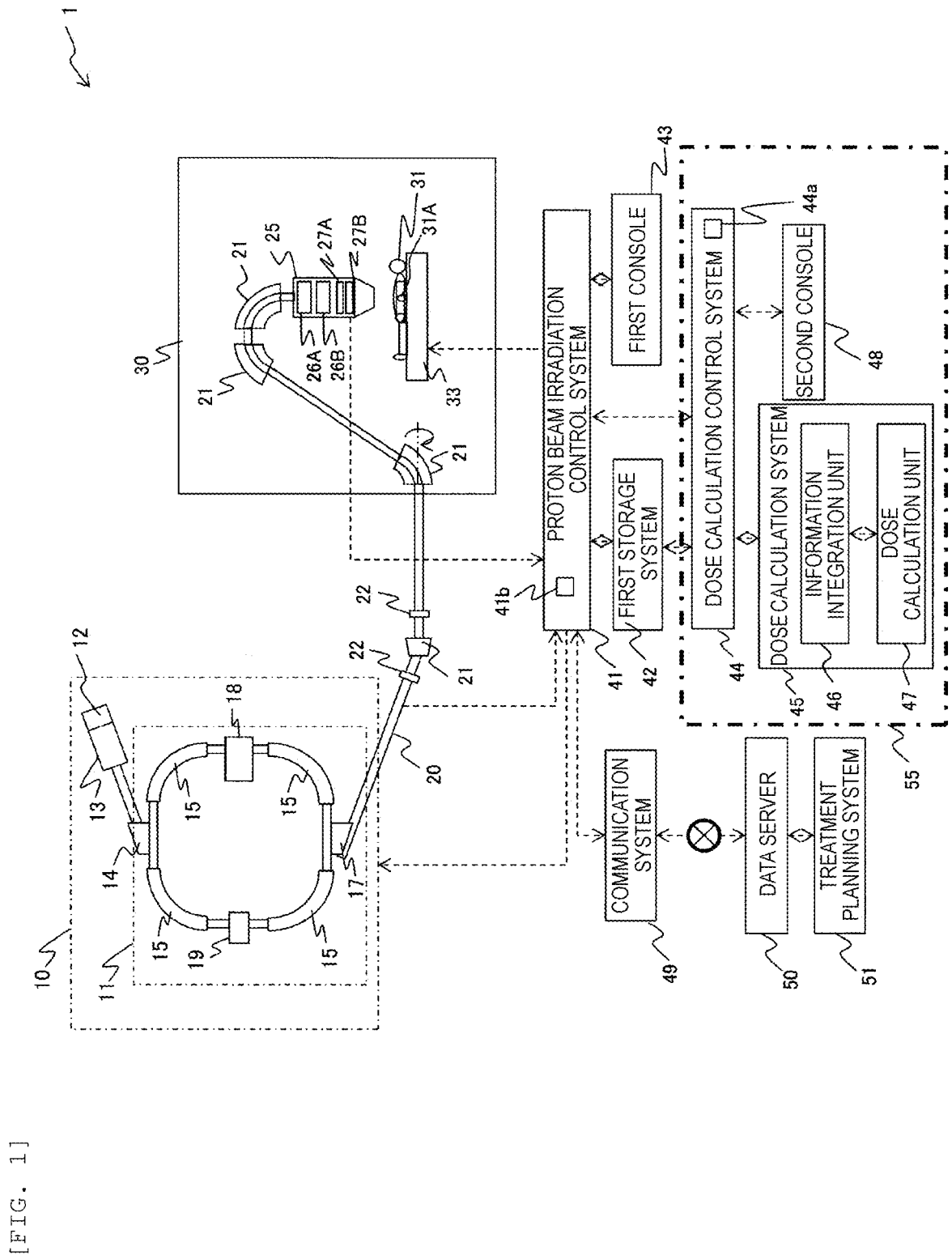

[FIG. 2]

| SPOT NUMBER | X [mm] | Y [mm] | SPOT DOSE [MU] |
|---|---|---|---|
| 1 | 5.5 | 0.0 | 0.02 |
| 2 | 0.3 | 0.0 | 0.03 |
| 3 | -4.9 | 0.0 | 0.01 |
| 4 | -10.1 | 0.0 | 0.02 |
| ... | | | |

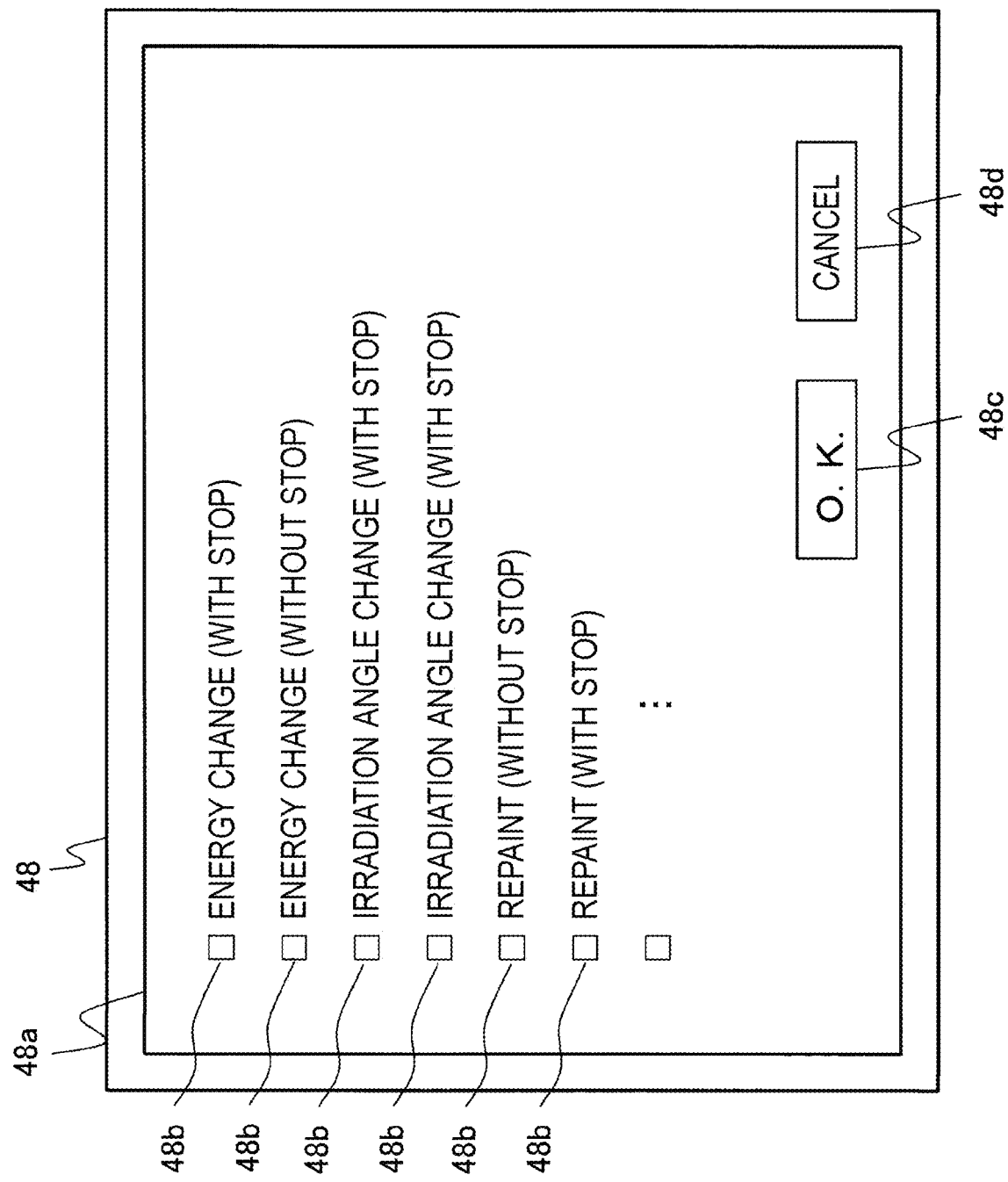

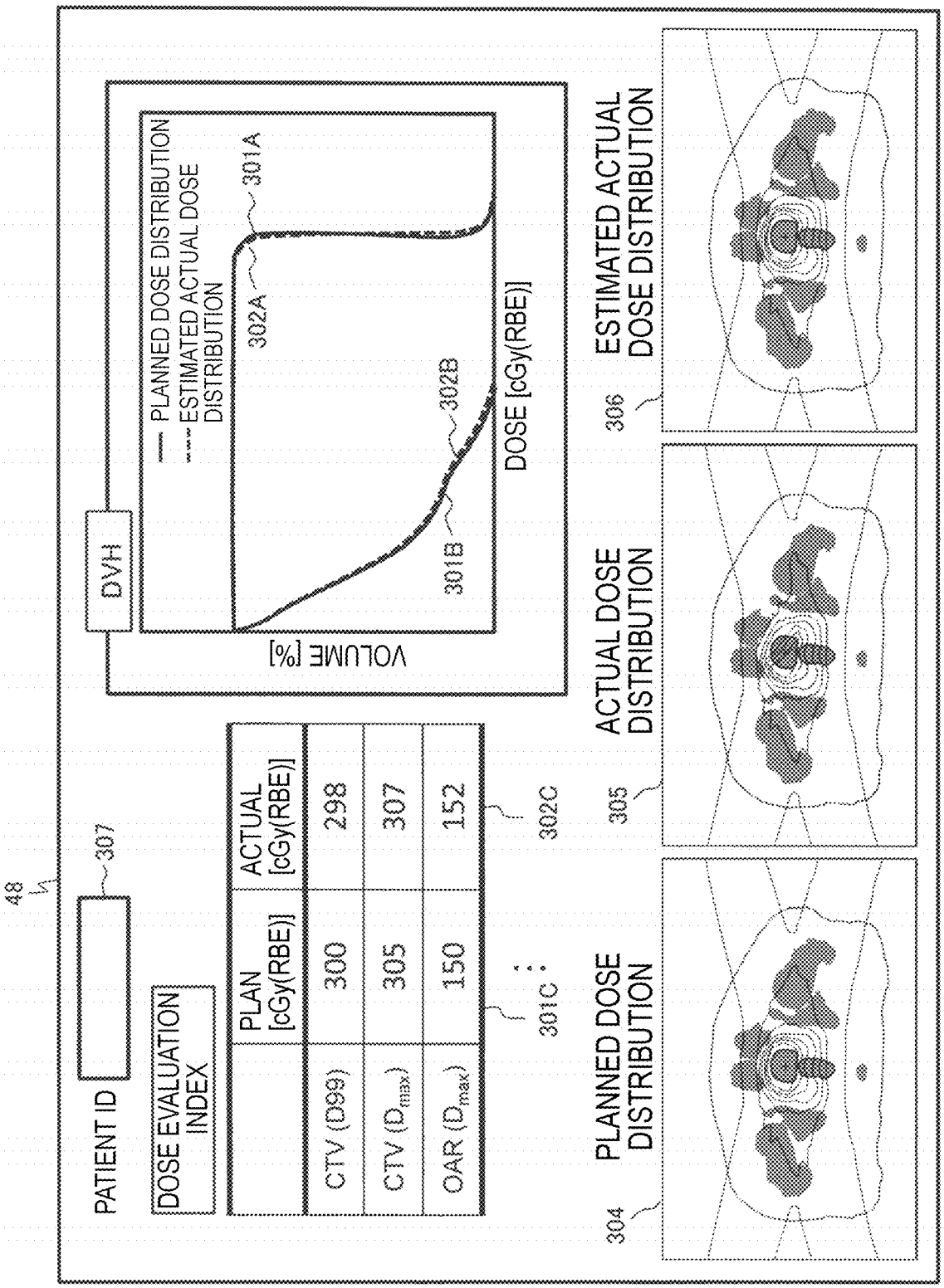

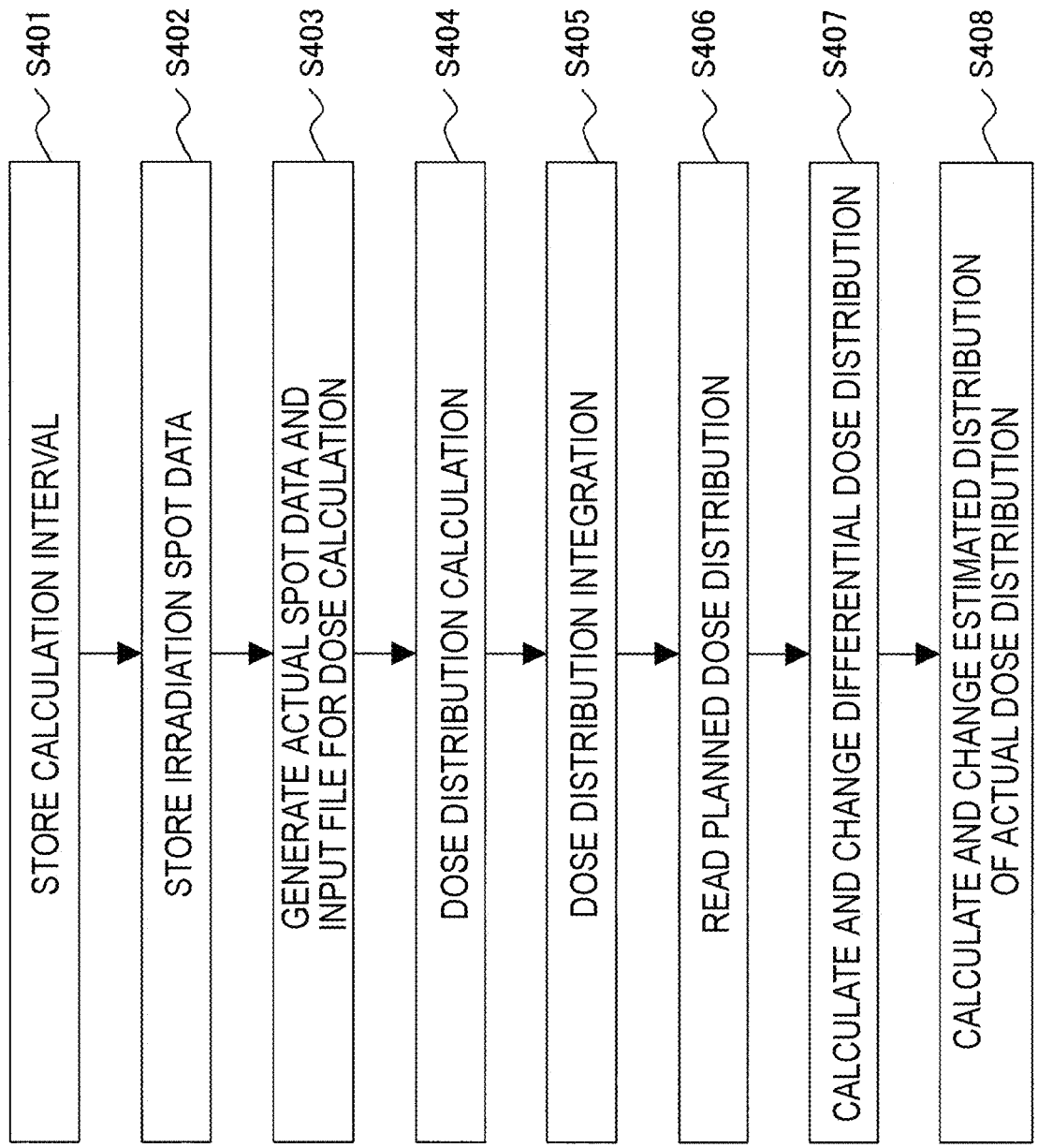
[FIG. 5]

| SPOT NUMBER | IRRADIATION TIME [ms] | X [mm] | Y [mm] | SPOT DOSE [MU] |
|---|---|---|---|---|
| 1 | 10010.0 | 5.5 | 0.0 | 0.02 |
| 2 | 10020.0 | 0.3 | 0.0 | 0.03 |
| 3 | 10030.0 | −4.9 | 0.0 | 0.01 |
| 4 | 10040.0 | −10.1 | 0.0 | 0.02 |
| ... | | | | |

[FIG. 8]

| X-RAY EXPOSURE NUMBER | EXPOSURE TIME [ms] | X [mm] | Y [mm] | Z [mm] | GATE SIGNAL |
|---|---|---|---|---|---|
| 1 | 10010.0 | 2.9 | 1.2 | 0.6 | OFF |
| 2 | 10020.0 | 2.0 | 1.0 | 0.4 | OFF |
| 3 | 10030.0 | 1.2 | 0.9 | 0.5 | ON |
| 4 | 10040.0 | 0.1 | 1.1 | 0.5 | ON |
| ... | | | | | |

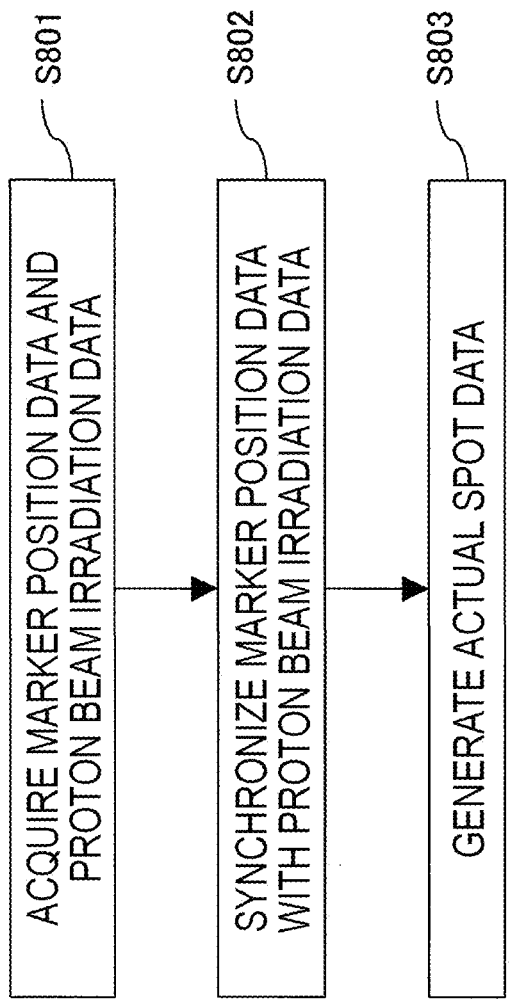

PARTICLE THERAPY SYSTEM, DOSE DISTRIBUTION EVALUATION SYSTEM, AND METHOD FOR OPERATING PARTICLE THERAPY SYSTEM

TECHNICAL FIELD

The present invention relates to a particle therapy system, a dose distribution evaluation system, and a method for operating the particle therapy system, which are used when treatment is performed by irradiating a target volume such as a tumor or the like with a particle beam.

BACKGROUND ART

As an example of a particle irradiation system that can display an irradiation position-related value associated with an irradiation position of a charged particle beam and an irradiation position-related value error in association with each other, JP-B-5496364 (PTL 1) describes that the particle irradiation system includes a data process system that displays the irradiation position-related value error which is an error from a target irradiation position-related value associated with a target irradiation position in an actual irradiation position-related value associated with an irradiation position of the charged particle beam, and an actual irradiation position-related value in association with each other on a display unit. The data process system includes a calculation unit that displays a target value display figure indicating the target irradiation position-related value and a measurement value display figure indicating the actual irradiation position-related value in a display coordinate which is a coordinate obtained by adding the target irradiation position-related value to a coordinate of the target irradiation position-related value and a coordinate in which the irradiation position-related value error is calculated with a deformation coefficient, and that displays a line segment connecting the measurement value display figure and the target value display figure.

CITATION LIST

Patent Literature

PTL 1: JP-B-5496364

SUMMARY OF INVENTION

Technical Problem

Radiation therapy is a treatment method that irradiates a target tumor with radiation and damages the tumor.

X-ray is the most widely used radiation for treatment, and there is also a high demand for particle therapy using a particle beam (a charged particle beam) represented by a proton beam and a carbon beam, which have high dose conformity.

Since the charged particle beam forms a dose distribution (Bragg curve) including a peak at a specific depth determined by energy of a beam, the particle therapy can significantly reduce a dose to a normal tissue existing at a position deeper than that of the tumor.

In the radiation therapy, a tumor region is irradiated with a desired dose so that the irradiation is performed as accurately as possible and is concentrated on a target volume as much as possible, thereby leading to an improvement in a therapeutic effect.

In the particle therapy, which is a type of the above-described radiation therapy, the use of a scanning irradiation method increases as a method of concentrating the dose on the target. The scanning irradiation method is a method in which a thin charged particle beam is bent by two sets of scanning magnets, and the thin charged particle beam is guided to any position in a plane to completely irradiate an inside of the tumor, such that a high dose is provided only to the tumor region.

The scanning irradiation method forms a dose distribution that matches a target shape by arranging a thin dose distribution referred to as a spot at each irradiation position. The arrangement of the spot is determined by a treatment planning system.

In the particle therapy system, the spot is arranged at a position planned by the treatment planning system within a range of irradiation accuracy guaranteed by a system.

Therefore, there is a slight difference between the actually arranged spot position and the planned spot position. The difference therebetween may cause occurrence of a high dose region and a low dose region in an integrated dose distribution. An influence of such irradiation accuracy on the dose distribution is referred to as an irradiation accuracy effect.

In the particle therapy system of the scanning irradiation method, the spots are formed sequentially, such that when the target moves during the irradiation, a relative positional relationship between the spots with respect to the target is changed.

In the scanning irradiation method, when the positional relationship between the spots is different from the plan, there is a possibility of causing the occurrence of the high dose region and the low dose region in the integrated dose distribution. An influence of such movement of the target on the dose distribution is referred to as an interaction effect. In order to reduce the interaction effect, when the scanning irradiation method is used for a moving target that moves during the irradiation, gate irradiation, in which irradiation is performed only when the target exists at a preset position (extraction permission range), is performed.

Here, in the radiation therapy including the particle therapy, the target is irradiated with a dose prescribed by a doctor for a plurality of days.

In order to reduce the number of treatment days, a single large dose irradiation, in which the dose is increased in one irradiation, is required. When the single large dose irradiation is performed, the irradiation accuracy effect and the interaction effect are grasped during irradiation, thereby making it possible to perform the safer radiation therapy.

Therefore, it is desirable to propose a material for determining whether the therapeutic effect can be obtained by visualizing the irradiation accuracy effect and the interaction effect to a medical staff such as a doctor, a radiologist, or the like during irradiation.

As an index to be proposed, it is desirable to propose a dose distribution to be used by the doctor in prescription, a dose volume histogram (DVH) illustrating a relationship between a volume of each organ and the target, or the like so that the medical staff can make an intuitive determination. Here, the DVH shows, as a graph, the dose of radiation with respect to the target and each volume of the normal tissue.

PTL 1 proposes the particle irradiation system that displays an irradiation position and an irradiation position error of each spot, or an irradiation parameter associated with the irradiation position and the error in association with each other.

However, in a technology described in PTL 1, while the position error of the spot position can be visualized, an influence of the spot error on the dose distribution (the irradiation accuracy effect) and the interaction effect cannot be visualized and proposed during irradiation, such that it is required to propose a more intuitive determination material.

The present invention provides a particle therapy system, a dose distribution evaluation system, and a method for operating the particle therapy system, in which it is possible to support a medical staff to quickly and appropriately make an intervention determination for treatment such as discontinuation of particle therapy, a change in conditions thereof, or the like in the process of particle irradiation.

Solution to Problem

The present invention includes a plurality of systems for solving the above-described problems, and one example thereof includes: a particle irradiation system for irradiating a target with a particle beam; an irradiation control system that controls the particle irradiation system; an irradiation amount measurement instrument that measures an irradiation amount of the particle beam emitted to the target; an irradiation position measurement instrument that measures a position of the particle beam emitted to the target; a dose calculation system that calculates an actual dose distribution emitted to the target by using measurement data of the irradiation amount measurement instrument and the irradiation position measurement instrument; a display system that displays an obtained dose distribution; and a dose calculation control system that sets a timing for calculating the actual dose distribution and controls a calculation state of the actual dose distribution, in which the dose calculation system calculates the actual dose distribution during irradiation based upon a calculation interval set by the dose calculation control system.

Advantageous Effects of Invention

According to the present invention, it is possible to support a medical staff to quickly and appropriately make an intervention determination for treatment such as discontinuation of particle therapy, a change in conditions thereof, or the like in the process of particle irradiation. An issue, a configuration, and an effect other than what is described above will be clarified by the description of the following embodiments.

BRIEF DESCRIPTION OF DRAWINGS

FIG. 1 is a diagram illustrating an example of an overall configuration of a proton beam therapy system according to an embodiment of the present invention.

FIG. 2 is a conceptual diagram of an example of proton beam irradiation data used for generating actual spot data in the proton beam therapy system of the present invention.

FIG. 3 is a diagram illustrating an example of a calculation interval setting screen for calculating an estimated actual dose distribution in the proton beam therapy system of the present invention.

FIG. 4 is a conceptual diagram illustrating an example of a screen that displays the estimated actual dose distribution or the like in the proton beam therapy system of the present invention.

FIG. 5 is a flow chart illustrating an example of a procedure for calculating a dose distribution during irradiation of a dose distribution evaluation system during irradiation in the proton beam therapy system of the present invention.

FIG. 6 is a diagram illustrating an example of an overall configuration of a proton beam therapy system corresponding to a moving body tracking irradiation method according to an embodiment of the present invention.

FIG. 7 is a conceptual diagram of an example of proton beam irradiation data in the proton beam therapy system corresponding to the moving body tracking irradiation method of the present invention.

FIG. 8 is a conceptual diagram of an example of marker position data that records X-ray exposure time and a target position in the proton beam therapy system corresponding to the moving body tracking irradiation method of the present invention.

FIG. 9 is a flow chart illustrating an example of a procedure for generating an actual spot in the proton beam therapy system corresponding to the moving body tracking irradiation method of the present invention.

DESCRIPTION OF EMBODIMENTS

Figure 6:
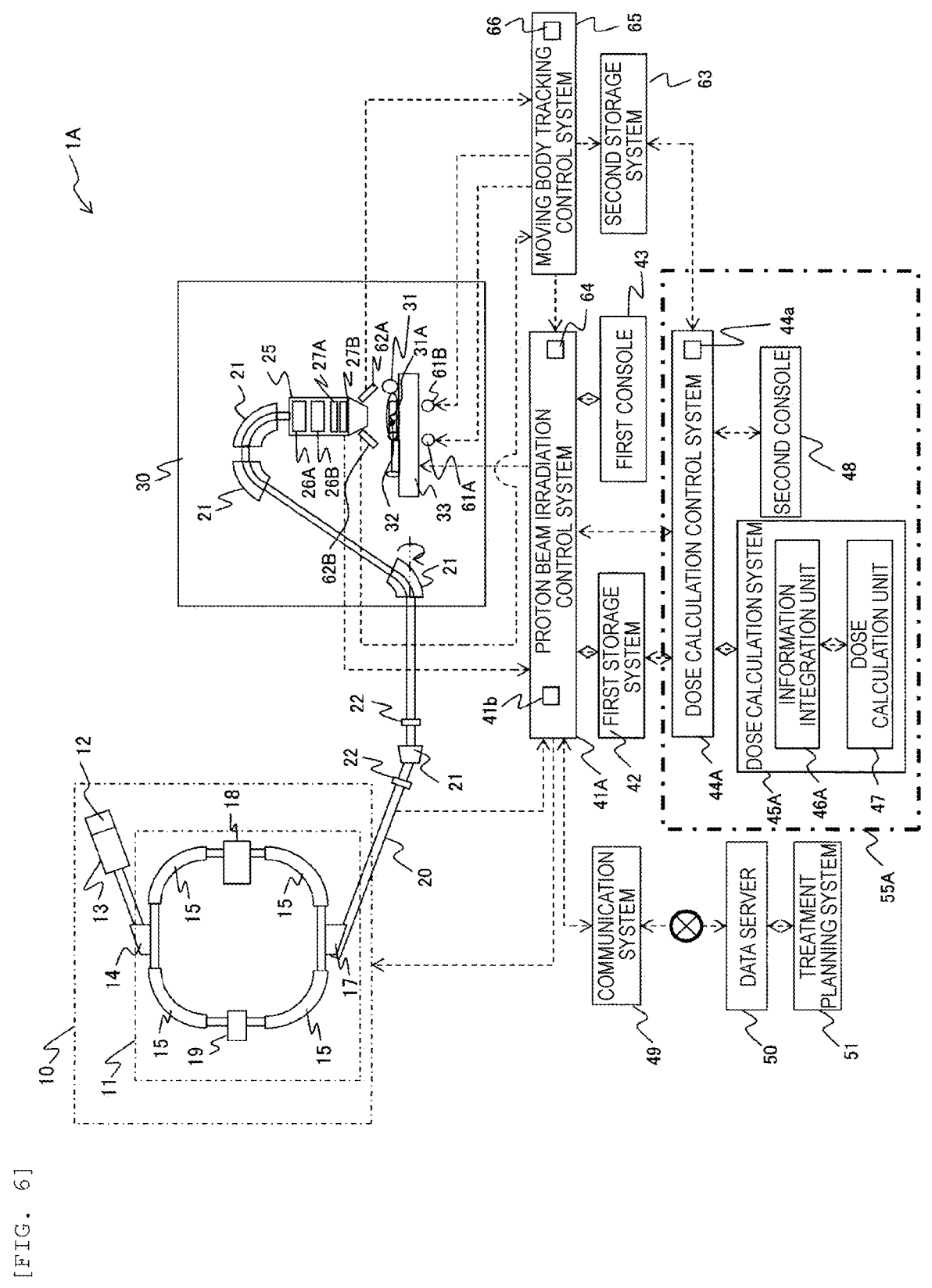

Embodiments of a particle therapy system, a dose distribution evaluation system, and a method for operating the particle therapy system of the present invention will be described with reference to FIGS. 1 to 9.

While the present invention can be applied to the particle therapy system such as a proton beam therapy system and a heavy particle therapy system such as a carbon beam, a helium beam, or the like, the proton beam therapy system will be described as an example in the embodiment.

Embodiments

An overall configuration of the proton beam therapy system and an operation thereof will be described with reference to FIGS. 1 to 5.

FIG. 1 is a diagram illustrating an example of an overall configuration of a proton beam therapy system according to the embodiment. FIG. 2 is a conceptual diagram of an example of proton beam irradiation data used for generating actual spot data. FIG. 3 is a diagram illustrating an example of a calculation interval setting screen for calculating an estimated actual dose distribution. FIG. 4 is a conceptual diagram illustrating an example of a screen that displays the estimated actual dose distribution or the like. FIG. 5 is a flow chart illustrating an example of a procedure for calculating a dose distribution during irradiation of a dose distribution evaluation system during irradiation.

As illustrated in FIG. 1, a proton beam therapy system 1 which is one of the embodiments of the present invention includes a proton beam generator 10, a beam transport system 20, an irradiation nozzle 25, a couch 33, a proton beam irradiation control system 41, and a first storage system 42, a first console 43, and a dose distribution evaluation system during irradiation 55.

A proton beam irradiation system for irradiating a target 31A in an irradiation target 31 with a proton beam includes the proton beam generator 10, the beam transport system 20, and the irradiation nozzle 25.

The proton beam generator 10 includes an ion source 12, a linac 13, and a synchrotron 11. The synchrotron 11 includes an injector 14, a bending magnet 15, a radiofrequency acceleration system 18, a radiofrequency extraction system 19, an extraction deflector 17, or the like. The ion source 12 is connected to the linac 13 and the linac 13 is connected to the synchrotron 11.

In the proton beam generator 10, the proton beam generated from the ion source 12 is accelerated at a previous stage by the linac 13 and is incident on the synchrotron 11. The proton beam further accelerated by the synchrotron 11 is extracted to the beam transport system 20.

The beam transport system 20 includes a plurality of quadrupole magnets 22 and a plurality of bending magnets 21, and connects the synchrotron 11 and the irradiation nozzle 25. A part of the beam transport system 20 and the irradiation nozzle 25 are installed in an approximately cylindrical gantry in a treatment room 30, and can rotate together with the gantry.

The proton beam extracted from the synchrotron 11 converges by the quadrupole magnet 22 while passing through an inside of the beam transport system 20, changes a direction thereof by the bending magnet 21, and is incident on the irradiation nozzle 25.

The irradiation nozzle 25 is a system for irradiating the target 31A with a particle beam, and includes two pairs of scanning magnets 26A and 26B, a dose monitor 27B, and a position monitor 27A. The two pairs of scanning magnets 26A and 26B are installed in directions orthogonal to each other, and deflect the proton beam so that the proton beam reaches a desired position in a plane perpendicular to a beam axis at a position of the target 31A.

The dose monitor 27B is a monitor that measures an irradiation amount of the proton beam emitted to the target 31A, and outputs a detected measurement value to the proton beam irradiation control system 41. The position monitor 27A is a monitor that indirectly measures an irradiation position of the proton beam emitted to the target 31A by detecting a position through which the proton beam emitted to the target 31A passes, and outputs the detected measurement value to the proton beam irradiation control system 41.

The proton beam passing through the irradiation nozzle 25 reaches the target 31A in the irradiation target 31. When treating a patient having cancer, the irradiation target 31 represents the patient, and the target 31A represents a tumor or the like.

A bed on which the irradiation target 31 is placed is referred to as the couch 33. The couch 33 can move in three-axis directions orthogonal to each other based upon an instruction from the proton beam irradiation control system 41, and can further move in so-called six-axis directions rotating around each axis. By the above-described movement and rotation, a position of the irradiation target 31 can be moved to a desired position.

The proton beam irradiation control system 41 is connected to the proton beam generator 10, the beam transport system 20, the irradiation nozzle 25, the couch 33, the first storage system 42, the first console 43, a dose calculation control system 44, a communication system 49, or the like, and controls an operation of each system forming the proton beam generator 10, the beam transport system 20, the irradiation nozzle 25, or the like.

The communication system 49 is connected to a data server 50 via a wired or wireless network, acquires an irradiation parameter (a gantry angle, planned spot data, or the like) generated by a treatment planning system 51 from the data server 50 via the network prior to irradiation, and stores the acquired irradiation parameter in the first storage system 42. During irradiation, the proton beam irradiation control system 41 stores measurement data outputted from the dose monitor 27B and the position monitor 27A in the first storage system 42 as proton beam irradiation data.

The first console 43 is a set of input and output systems, and is formed of a display system such as a display or the like and an input system such as a keyboard or the like. The first console 43 displays information based upon a signal acquired from the proton beam irradiation control system 41. The first console 43 also receives an input from a medical staff who operates the proton beam therapy system 1 and transmits various control signals to the proton beam irradiation control system 41.

In the first storage system 42, during irradiation of the proton beam, for each irradiation of the spot, an arrival position of the proton beam converted from a measurement result of the position monitor 27A and a spot dose corresponding to the irradiation amount measured by the dose monitor 27B are stored as the proton beam irradiation data. An example of the stored proton beam irradiation data is illustrated in FIG. 2. One line in FIG. 2 corresponds to data for one spot.

The dose distribution evaluation system during irradiation 55 is formed of the dose calculation control system 44, a dose calculation system 45, and a second console 48, and is a system that calculates the dose distribution of the particle beam emitted to the target 31A during irradiation.

The dose calculation control system 44 controls an output of the proton beam irradiation data from the first storage system 42, calculation of the dose distribution by the dose calculation system 45, and a display of the dose distribution by the second console 48 during the proton beam irradiation. Particularly, the dose calculation control system 44 of the embodiment sets a timing for calculating an actual dose distribution, and controls a calculation state of the actual dose distribution.

The dose calculation control system 44 is connected to the proton beam irradiation control system 41, the first storage system 42, the dose calculation system 45, and the second console 48.

The second console 48 is a set of input and output systems in the same manner as that of the first console 43, and is formed of a display system such as a display or the like and an input system such as a keyboard or the like.

The dose calculation control system 44 including a calculation interval setting unit 44a outputs the proton beam irradiation data into the first storage system 42 at an interval set by the calculation interval setting unit 44a, and then calculates the actual dose distribution by using the dose calculation system 45. Data related to a patient such as CT data or the like required for the dose calculation is acquired from the data server 50 via a network via the communication system 49 connected to the proton beam irradiation control system 41.

Hereinafter, setting of a calculation interval will be described with reference to FIG. 3.

As illustrated in FIG. 3, the calculation interval setting unit 44a displays a setting screen 48a on the second console 48. The medical staff operates the second console 48 to select a plan division method from any one of "every time an irradiation angle is changed", "every time energy is changed (a deep portion/a shallow portion, or the like)", and "every time repaint that changes irradiation order is performed so that irradiation is performed a plurality of times to irradiate the whole portion" in a selection region 48b displayed on the setting screen 48a of the second console 48, and press an O.K. button 48c. In the case of cancellation, the medical staff presses a cancel button 48d.

Although details will be described later, the selection region 48b of the setting screen 48a has a function of enabling each division plan to select whether to execute a mode of allowing the proton beam irradiation control system 41 to execute control of waiting for the start of the proton beam irradiation until the dose calculation control system 44 receives a completion signal of the dose calculation.

The dose calculation system 45 is formed of an information integration unit 46 and a dose calculation unit 47, and calculates, during the proton beam irradiation, the dose distribution (the actual dose distribution) actually emitted to the target 31A by using the proton beam irradiation data measured by the dose monitor 27B and the position monitor 27A stored in the first storage system 42. The dose calculation system 45 calculates the actual dose distribution during irradiation based upon the calculation interval set by the calculation interval setting unit 44a of the dose calculation control system 44 described above.

The information integration unit 46 generates a format of the proton beam irradiation data used for the dose calculation (actual spot data) from the proton beam irradiation data acquired from the first storage system 42. In the case of the irradiation position and the irradiation amount of the actual spot data, a value described in the proton beam irradiation data is used, and in the case of the energy, a setting value of the energy of the proton beam (a value of the planned spot data) stored in the first storage system 42 is used.

After generating the actual spot data, the information integration unit 46 generates an input file for dose calculation based upon the irradiation parameter stored in the first storage system 42 and the patient data acquired from the data server 50.

The dose calculation unit 47 calculates the dose distribution by using the actual spot data and the input file for dose calculation generated by the information integration unit 46. The dose calculation unit 47 calculates the dose distribution for each calculation interval set by the calculation interval setting unit 44a.

Continuously, the dose calculation system 45 sequentially integrates the dose distribution calculated by the dose calculation unit 47 and calculates the actual dose distribution. The actual dose distribution is displayed on the second console 48 by the dose calculation control system 44. The dose calculation control system 44 can display a planned dose distribution and the actual dose distribution side by side on the second console 48 so that the medical staff can compare the planned dose distribution generated by treatment planning with the actual dose distribution. The screen or the like displayed on the second console 48 will be described in detail later with reference to FIGS. 3 and 4.

The planned dose distribution may be acquired from the data server 50 via the network via the communication system 49 connected to the proton beam irradiation control system 41, and may be calculated and acquired based upon the planned spot data stored in the first storage system 42. In the following, a case in which the planned dose distribution is acquired from the data server 50 will be described as an example.

Here, in a particle therapy system of a related art, the actual dose distribution is calculated by integrating the dose distribution calculated based upon the actual spot data. Therefore, until the irradiation of all the proton beams is completed, the planned dose distribution and the actual dose distribution cannot be compared and evaluated by using a dose evaluation index such as a DVH or the like used for prescription by a doctor or the like.

In the present embodiment, the dose calculation system 45 calculates the actual dose distribution and appropriately displays the calculated actual dose distribution on the second console 48 so that the dose evaluation index such as the DVH or the like can be used when the actual dose distribution and the planned dose distribution are evaluated during the proton beam irradiation. The dose calculation system 45 further has a function of calculating an estimated actual dose distribution 306 (an estimated distribution of the actual dose distribution, refer to FIG. 4) as the dose distribution formed by currently ongoing irradiation based upon the actual dose distribution, and displaying the estimated actual dose distribution 306 on the second console 48.

More specifically, the dose calculation system 45 calculates a differential dose distribution between the planned dose distribution and the actual dose distribution at the calculation interval being recorded in irradiation planning for each calculation interval set by the dose calculation control system 44 during the proton beam irradiation. After that, the dose calculation system 45 calculates the estimated actual dose distribution 306 by integrating the differential dose distribution for each calculation interval with respect to a planned dose distribution 304 (refer to FIG. 4) formed by the currently ongoing irradiation.

The estimated actual dose distribution 306 is used, thereby making it possible to compare with the planned dose distribution by using the dose evaluation index such as the DVH or the like during irradiation.

The dose calculation system 45 displays the estimated actual dose distribution, the planned dose distribution, and the dose evaluation index such as the DVH or the like calculated from such distributions on the second console 48.

FIG. 4 shows an example of a display screen of the second console 48. As illustrated in FIG. 4, the "planned dose distribution 304" displayed on the second console 48 is a distribution based upon prior treatment planning. An "actual dose distribution 305" is a dose distribution calculated by using the actual spot data irradiated up to a display timing. The "estimated actual dose distribution 306" is a dose distribution when it is assumed that a remaining spot is irradiated as planned in addition to the actual dose distribution 305.

DVH 302A of the target 31A and DVH 302B of a dangerous organ are displayed on the second console 48 as the dose evaluation index calculated from the estimated actual dose distribution 306. DVH 301A of the target 31A and DVH 301B of the dangerous organ are compared and displayed thereon as the planned dose evaluation index calculated from the planned dose distribution 304.

The second console 48 displays various dose evaluation indexes such as D99 which represents a dose value with respect to a volume of 99% of a clinical target volume (CTV) defined by CT, MRI, visual inspection, or the like in a range that considers micro-infiltration or the like in a gross tumor volume which is a range where cancer apparently exists, $D_{max}$ (depth of dose maximum: maximum depth) which is a depth at which the maximum absorbed dose is generated along the beam axis when the beam is incident on the patient, and $D_{max}$ of a peripheral organ at risk (OAR) which is a region where formation of the dose distribution should be avoided as much as possible.

For example, as illustrated in FIG. 4, various planned dose evaluation indexes 301C such as D99 and $D_{max}$ of CTV and $D_{max}$ of OAR calculated from the planned dose distribution 304 are displayed. Next to the planned dose evaluation index 301C, various dose evaluation indexes 302C such as D99 and $D_{max}$ of CTV and $D_{max}$ of OAR calculated from the estimated actual dose distribution 306 are displayed.

Although not illustrated in the drawing, the second console 48 can further display various dose evaluation indexes calculated from dose distributions such as a maximum dose, a minimum dose, tumor control probability (TCP), normal tissue complication probability (NTCP), or the like.

The second console 48 can further display a distribution in which the actual dose distribution is integrated with the actual dose distribution calculated in the past, a dose distribution obtained by scaling the distribution, a dose evaluation index obtained from these dose distributions, or the like.

As illustrated in FIG. 4, a selection field 307 of ID that specifies the irradiation target, which is necessary for the calculation of various dose evaluation indexes described above, can also be displayed and set on the second console 48.

The proton beam irradiation control system 41, the first storage system 42, the dose calculation control system 44 in the dose distribution evaluation system during irradiation 55, and the dose calculation system 45 are respectively formed of a computer or the like. The computer forming the above-described systems is provided with a CPU, a memory, an interface, or the like, and control of an operation of each system, various calculation processes described later, or the like are executed based upon various programs. The programs are stored in an internal recording medium, an external recording medium, and the data server 50 in each configuration, and are read and executed by the CPU.

Operation control processes may be integrated into one program, may be divided into a plurality of programs, and may be a combination thereof. A part of the program or all the programs may be realized by dedicated hardware, and may be modularized. Various programs may be installed in each system from a program distribution server, an internal storage medium, and an external recording medium.

Respective device and system are not required to be independent, and two or more devices and systems may be integrated and shared, and only the process may be shared. It can be assumed that at least a part of the configuration is connected via a wired or wireless network.

Referring back to FIG. 1, the proton beam irradiation control system 41 includes an irradiation sequence division unit 41b that divides the planned spot data based upon a division unit.

In the case of performing repaint irradiation in which irradiation is performed with the planned dose by irradiating the same position a plurality of times and averaging the same position, the irradiation sequence division unit 41b divides the planned spot data in repaint unit and generates divided spot data.

In the embodiment, while a calculation result of the dose distribution is displayed on the second console 48, an input content and a display content of the second console 48 may be displayed on the first console 43, and the first console 43 and the second console 48 may be unified.

Next, a procedure for emitting the proton beam and a procedure for calculating the actual dose distribution during the proton beam irradiation will be described with reference to FIG. 5.

First, the irradiation target 31 is fixed on the couch 33. After that, the couch 33 is moved to move the irradiation target 31 to a predetermined position. Here, a captured image is imaged by using an X-ray imaging system (corresponding to X-ray generators for imaging 61A and 61B and X-ray measurement instruments 62A and 62B in FIG. 6), thereby confirming that the irradiation target 31 is moved to the predetermined position.

When an irradiation preparation button on the first console 43 is pressed by a medical staff, the proton beam irradiation control system 41 reads the irradiation parameter from the first storage system 42. The medical staff presses a gantry rotation button from the first console 43 to rotate the gantry up to a predetermined angle according to the gantry angle described in the read irradiation parameter.

Continuously, the medical staff presses a patient information reading button in order to acquire patient information such as a patient CT image or the like corresponding to the irradiation target 31 from the second console 48. When the patient information read button is pressed, the dose calculation control system 44 acquires the patient information from the data server 50 via a wired or wireless network via the proton beam irradiation control system 41 and the communication system 49. The patient information such as the patient CT image or the like acquired from the data server 50 is displayed on the second console 48.

After that, the medical staff sets the calculation interval for calculating the actual dose distribution from the second console 48. When the calculation interval is set by the medical staff, the dose calculation control system 44 stores the set calculation interval in the first storage system 42 (step S401). Hereinafter, a case in which an energy change unit is selected as the calculation interval will be described as an example.

After the gantry is rotated, when it is determined by the medical staff that an irradiation start button on the first console 43 is pressed, the proton beam irradiation control system 41 accelerates the proton beam up to energy for first irradiation based upon information of the energy, the irradiation position, and the irradiation amount read from the first storage system 42.

Specifically, the proton beam irradiation control system 41 controls the ion source 12 and the linac 13, accelerates the proton beam generated by the ion source 12 at the previous stage by the linac 13, and causes the accelerated proton beam to be incident on the synchrotron 11.

Next, the proton beam irradiation control system 41 controls the synchrotron 11, and accelerates the incident proton beam up to the energy for the first irradiation. The proton beam orbiting the synchrotron 11 is accelerated by radiofrequency from the radiofrequency acceleration system 18.

In parallel, the proton beam irradiation control system 41 controls excitation amounts of the bending magnet 21 and the quadrupole magnet of the beam transport system 20 so that the proton beam of the energy for the first irradiation can reach the irradiation nozzle 25 from the synchrotron 11. Excitation amounts of the two scanning magnets 26A and 26B in the irradiation nozzle 25 are set so that the proton beam reaches a spot position to be first irradiated in the irradiation parameter from the first storage system 42.

After the settings are completed, the proton beam irradiation control system 41 applies radiofrequency to the radiofrequency extraction system 19, and starts to extract the proton beam. When the radiofrequency is applied to the radiofrequency extraction system 19, a part of the proton beam orbiting in the synchrotron 11 passes through the extraction deflector 17 and reaches the irradiation nozzle 25 via the beam transport system 20. The proton beam reaching the irradiation nozzle 25 is scanned by the two scanning magnets 26A and 26B, passes through the dose monitor 27B and the position monitor 27A, and reaches the target 31A in the irradiation target 31, thereby forming the dose distribution.

The irradiation amount for each spot is registered as the irradiation parameter acquired from the first storage system 42, such that when the irradiation amount measured by the dose monitor 27B reaches a registered value, the proton beam irradiation control system 41 controls the radiofrequency for extraction to stop the extraction of the proton beam.

After the proton beam is extracted, the proton beam irradiation control system 41 calculates an arrival position of the proton beam at the position of the target 31A from position information of the proton beam measured by the position monitor 27A, and confirms that a difference between the position registered as the irradiation parameter and the calculated arrival position is within tolerance.

After the proton beam is extracted, the proton beam irradiation control system 41 stores time when the proton beam is emitted, an irradiation position, and an irradiation amount as illustrated in FIG. 2 as the proton beam irradiation data. The irradiation position is a value obtained by converting the position information of the proton beam measured by the position monitor 27A into the arrival position of the proton beam at the position of the target 31A, and the irradiation amount is a value of the spot dose obtained from a value measured by the dose monitor 27B. The data for one spot corresponds to one line in FIG. 2.

In order to irradiates the next spot, the proton beam irradiation control system 41 sets the excitation amounts of the two scanning magnets 26A and 26B so that the proton beam reaches the position registered as the irradiation parameter. After the setting is completed, the proton beam irradiation control system 41 controls the radiofrequency for extraction to start the extraction of the proton beam.

Spot irradiation is repeatedly performed, and when all the spot irradiation, in which irradiation is performed with the first energy, is completed, the proton beam irradiation control system 41 controls the synchrotron 11 to decelerate the proton beam, and starts preparation for irradiation of the proton beam of the next energy.

When the calculation interval recorded in the first storage system 42 is reached, the proton beam irradiation control system 41 transmits an output instruction signal of log data to the dose calculation control system 44. The embodiment will describe, as an example, a case in which each energy change is given as the calculation interval.

When the proton beam irradiation control system 41 starts the preparation for irradiation of the proton beam of the next energy, the dose calculation control system 44 receives the output instruction signal of the log data, and stores irradiation spot data stored in the first storage system 42 in a memory of the dose calculation control system 44 (step S402).

After that, the dose calculation control system 44 transmits an output completion signal of the log data to the dose calculation system 45. When the dose calculation system 45 receives the output completion signal of the log data, the information integration unit 46 in the dose calculation system 45 reads the irradiation spot data stored in the memory of the dose calculation control system 44, and generates the actual spot data and the input file for dose calculation (step S403).

After the information integration unit 46 generates the actual spot data and the input file for dose calculation, the dose calculation unit 47 calculates the dose distribution by using the actual spot data (step S404). When there is an actual dose distribution already calculated, the dose distribution calculated in step S404 is integrated (step S405).

When the calculation of the actual dose distribution is completed, the dose calculation system 45 reads the planned dose distribution corresponding to the calculation interval set by the medical staff (step S406), and calculates a differential dose distribution from the planned dose distribution (step S407).

Continuously, the dose calculation system 45 adds the differential dose distribution to the planned dose distribution corresponding to a planned plan, and calculates the estimated actual dose distribution and the corresponding dose evaluation index (step S408).

After calculating the estimated actual dose distribution, the dose calculation system 45 transmits the completion signal of the dose calculation to the dose calculation control system 44. After receiving the completion signal of the dose calculation, the dose calculation control system 44 displays the actual dose distribution, the estimated actual dose distribution, and the corresponding dose evaluation index on the second console 48. The screen as illustrated in FIG. 4 is displayed by the above-described process.

While confirming the estimated actual dose distribution and the corresponding dose evaluation index displayed on the second console 48, the medical staff such as a doctor or the like can make an intervention determination for treatment such as discontinuation of irradiation or the like during irradiation.

When the preparation for irradiation of the proton beam of the next energy is completed, in the same manner as that of the case of the first energy, the proton beam irradiation control system 41 controls the ion source 12 and the linac 13, causes the proton beam to be incident on the synchrotron 11, controls the synchrotron 11, and accelerates the incident proton beam up to second energy.

The proton beam irradiation control system 41 controls the beam transport system 20 and the two scanning magnets 26A and 26B to continuously perform the spot irradiation, and stores the position information of the proton beam measured by the position monitor 27A and the irradiation amount measured by the dose monitor 27B in the first storage system 42.

The dose calculation control system 44 waits until receiving an output instruction signal of the next log data.

When receiving the output instruction signal of the next log data, the dose calculation control system 44 outputs the irradiation spot data stored between the reception of the output instruction signal of the previous log data and the reception of the output instruction signal of the next log data to the first storage system 42. After that, the dose calculation control system 44 performs the processes from step S402 to step S407 described above, and updates the actual dose distribution and the differential dose distribution.

Continuously, the dose calculation system 45 updates the estimated actual dose distribution by using the updated differential dose distribution, and calculates the dose evaluation index corresponding to the estimated actual dose distribution.

After updating the estimated actual dose distribution, the dose calculation system 45 transmits the completion signal of the dose calculation to the dose calculation control system 44. The dose calculation control system 44 displays the updated distribution and dose evaluation index on the second console 48.

On the other hand, when receiving the output instruction signal of the next log data before receiving the completion signal of the dose calculation, the dose calculation control system 44 outputs the irradiation spot data stored between the reception of the output instruction signal of the previous log data and the reception of the output instruction signal of the next log data to the first storage system 42, and waits until receiving the completion signal of the dose calculation.

The dose calculation control system 44 transmits the output completion signal of the log data to the dose calculation system 45 after receiving the completion signal of the dose calculation. After that, the dose calculation control system 44 performs the processes from step S402 to step S407 described above, and updates the actual dose distribution and the differential dose distribution.

Continuously, the dose calculation system 45 updates the estimated actual dose distribution by using the updated differential dose distribution, and calculates the dose evaluation index corresponding to the estimated actual dose distribution.

After updating the estimated actual dose distribution, the dose calculation system 45 transmits the completion signal of the dose calculation to the dose calculation control system 44. The dose calculation control system 44 displays the updated distribution and dose evaluation index on the second console 48.

The proton beam irradiation control system 41 can be provided with a mode in which the start of the proton beam irradiation is waited until the dose calculation control system 44 receives the completion signal of the dose calculation, so that a situation, in which the dose calculation control system 44 receives the output instruction signal of the log data before the dose calculation control system 44 receives the completion signal of the dose calculation, does not occur. The proton beam irradiation control system 41 can be provide with a function of switching between the aforementioned standby mode and a mode in which irradiation is continuously performed without waiting.

Switching between the above-described modes can be selected on the setting screen 48*a* of the second console 48 illustrated in FIG. 3 described above. For example, in the selection region 48*b* of each division plan, when a portion of the selection region 48*b* described with "(with stop)" is selected, the standby mode becomes enabled, and when a portion thereof not described with "(with stop)" is selected, the mode in which irradiation is continuously performed without waiting becomes enabled.

When irradiation of the proton beam is interrupted by interlocking, an instruction from the medical staff, or the like during irradiation of the proton beam, the proton beam irradiation control system 41 transmits a forced stop signal to the dose calculation control system 44.

When receiving the forced stop signal, the dose calculation control system 44 outputs the irradiation spot data stored in the first storage system 42 to the first storage system 42. After that, when the completion signal of the dose calculation is not received, the dose calculation control system 44 waits until the completion signal of the dose calculation is received and then transmits the output completion signal of the log data to the dose calculation system 45. After that, the dose calculation control system 44 performs the processes from step S402 to step S407, and updates the actual dose distribution and the differential dose distribution.

Continuously, the dose calculation system 45 updates the estimated actual dose distribution by using the updated differential dose distribution, and calculates the dose evaluation index corresponding to the estimated actual dose distribution.

After updating the estimated actual dose distribution, the dose calculation system 45 transmits the completion signal of the dose calculation to the dose calculation control system 44. The dose calculation control system 44 displays the updated distribution and dose evaluation index on the second console 48.

The above-described operation is repeated to irradiate all the planned spot data read from the first storage system 42. When the irradiation is completed, information of the irradiation completion is transmitted from the proton beam irradiation control system 41 to the first console 43, and the information of the irradiation completion is displayed on the first console 43.

When the target 31A is irradiated from a plurality of directions, the angle of the gantry and the position of the couch 33 are changed, and then the medical staff presses the irradiation preparation button and repeats the irradiation of the proton beam in the same manner.

<Effect>

Next, an effect of the embodiment will be described.

The dose distribution evaluation system during irradiation 55 of the proton beam therapy system 1 according to the embodiment described above includes: the dose calculation system 45 that calculates the actual dose distribution emitted to the target 31A by using the measurement data of the dose monitor 27B and the position monitor 27A; the second console 48 that displays the obtained dose distribution; and the dose calculation control system 44 that sets the timing for calculating the actual dose distribution and controls the calculation state of the actual dose distribution. The dose calculation system 45 calculates the actual dose distribution during irradiation based upon the calculation interval set by the dose calculation control system 44.

According to the present invention as described above, the actual dose distribution in consideration of the irradiation accuracy effect can be calculated in an irradiation process of the particle beam. Therefore, it is possible to propose, to the medical staff, a determination material useful for the intervention determination for treatment such as the discontinuation of the particle therapy and a change in conditions thereof, or the like during irradiation. Accordingly, it is possible to support the medical staff to quickly and appropriately make the intervention determination for treatment during irradiation. Examples of intervention may include discontinuation of irradiation, fine adjustment of an irradiation amount of unirradiated divided spot data, or the like.

The dose calculation system 45 can calculate the estimated actual dose distribution 306 as the dose distribution formed by the currently ongoing irradiation based upon the actual dose distribution, and can display the estimated actual dose distribution 306 on the second console 48, thereby making it possible to propose the dose distribution that can be obtained by the currently ongoing irradiation. Therefore, it is possible to propose the determination material more useful for the intervention determination to the medical staff, and to more strongly support the medical staff to make quicker and more accurate determination.

Particularly, the dose calculation system 45 calculates the estimated actual dose distribution 306 by calculating the differential dose distribution between the planned dose distribution 304 and the actual dose distribution at the calculation interval recorded in the irradiation plan for each calculation interval set by the dose calculation control system 44, and by integrating the differential dose distribution for each calculation interval with respect to the planned dose distribution 304 formed by the currently ongoing irradiation, such that the estimated actual dose distribution can be calculated without causing an excessive calculation load. Therefore, it is possible to more easily realize accurate support for the medical staff.

The dose calculation system 45 displays the dose evaluation indexes 302A, 302B, and 302C calculated from the estimated actual dose distribution 306 on the second console 48, compares the estimated actual dose distribution 306 and the planned dose distribution 304 formed by the currently ongoing irradiation and displays a comparison result on the second console 48, and compares the dose evaluation indexes 302A, 302B, and 302C and the planned dose evaluation indexes 301A, 301B, and 301C calculated from the planned dose distribution 304 and displays a comparison result on the second console 48, thereby making it possible to propose the determination material more useful for the intervention determination to the medical staff.

The irradiation sequence division unit 41b that divides the irradiation sequence into a plurality of sequences in repaint unit is further provided, such that evaluation of the actual dose distribution during irradiation can be performed in repaint unit (divided spot unit). As a result, the medical staff such as a doctor or the like can make the intervention determination for treatment in repaint unit while observing the calculation result of the actual dose distribution displayed on the second console 48.

The dose calculation system can select the mode in which the particle irradiation is stopped until the calculation of the actual dose distribution is completed, and the mode in which the particle irradiation is continuously performed even though the calculation of the actual dose distribution is not completed in cooperation with the proton beam irradiation control system 41, such that irradiation can be appropriately performed while confirming the actual dose distribution or the like, and irradiation completion without the interruption of irradiation can be prioritized, thereby making it possible to flexibly perform the irradiation depending on a situation.

<Modification>

Next, as a modification of the present invention, a proton beam therapy system 1A corresponding to a moving body tracking irradiation method will be described with reference to FIGS. 6 to 9.

FIG. 6 is a diagram illustrating an overall configuration of the proton beam therapy system corresponding to the moving body tracking irradiation method according to the embodiment of the present invention, FIG. 7 is a conceptual diagram of proton beam irradiation data in the proton beam therapy system corresponding to the moving body tracking irradiation method, FIG. 8 is a conceptual diagram of marker position data that records X-ray exposure time and the position of the target 31A, and FIG. 9 is a flow chart illustrating a procedure for generating an actual spot in the proton beam therapy system corresponding to the moving body tracking irradiation method.

When the proton beam irradiation is performed on the target 31A that moves by breathing or the like during irradiation, gate irradiation is often used. Hereinafter, the proton beam therapy system 1A corresponding to a gate irradiation method will be described. First, the overall configuration of the system will be described with reference to FIG. 6.

At the time of performing the gate irradiation, it is important to evaluate an interaction effect, which is an influence of the movement of the target 31A on the dose distribution, during irradiation.

The proton beam therapy system 1A according to the embodiment illustrated in FIG. 6 includes a moving body tracking system and a system related to the moving body tracking system in addition to the configuration of the proton beam therapy system 1 described in FIG. 1.

The moving body tracking system includes a tracking target position measurement unit that measures a position of a marker 32 irradiated with the particle beam, a moving body tracking control system 65, and a second storage system 63.

The tracking target position measurement unit includes a first X-ray imaging system formed of the X-ray generator for imaging 61A and the X-ray measurement instrument 62A for acquiring a captured image of the marker 32 in the irradiation target 31; and a second X-ray imaging system formed of the X-ray generator for imaging 61B and the X-ray measurement instrument 62B for acquiring the captured image of the marker 32 from a direction different from that of the first X-ray imaging system.

The two sets of the first X-ray imaging system and the second X-ray imaging system are installed so that respective X-ray paths thereof intersect. The first X-ray imaging system and the second X-ray imaging system are desirably installed in directions orthogonal to each other, and may not be installed in directions orthogonal to each other. The first X-ray imaging system and the second X-ray imaging system are not necessarily required to be arranged inside the gantry, and may be arranged at a fixed place such as a ceiling, a floor, or the like. The X-ray imaging system is not required to be formed of two sets, and may be formed of one set or three or more sets.

The moving body tracking control system 65 is connected to the X-ray generators for imaging 61A and 61B, the X-ray measurement instruments 62A and 62B, and the second storage system 63.

The moving body tracking control system 65 outputs an imaging signal to the X-ray generators for imaging 61A and 61B. The moving body tracking control system 65 obtains a three-dimensional position of the marker 32 in the irradiation target 31 based upon an X-ray image inputted from the X-ray measurement instruments 62A and 62B, thereby obtaining a three-dimensional position of the target 31A. Next, the moving body tracking control system 65 determines whether the obtained three-dimensional position of the target 31A is within a predetermined range, and when determining that the three-dimensional position thereof is within the predetermined range, the moving body tracking control system 65 outputs a signal for allowing the proton beam irradiation control system 41A to extract the particle beam. On the other hand, when determining that the three-dimensional position of the target 31A is not within the predetermined range, the moving body tracking control system 65 does not permit the proton beam irradiation without outputting a special signal to the proton beam irradiation control system 41A.

The proton beam irradiation control system 41A controls ON/OFF of the irradiation of the particle beam based upon the signal to be generated by the moving body tracking control system 65.

The moving body tracking control system 65 of the modification includes a tracking time recording unit 66 that stores time (tracking time) of exposure to the X-ray for each imaging of the X-ray, and stores a calculation result of the position of the marker 32, a state of a gate signal, and corresponding time in the second storage system 63 as marker position data as illustrated in FIG. 7. In FIG. 7, an item of irradiation time is added to marker position data illustrated in FIG. 2.

In order to calculate the interaction effect, it is important to record the irradiation time of each spot to be irradiated.

Therefore, the proton beam irradiation control system 41A measures the irradiation amount of the proton beam with the dose monitor 27B, and associates time when the irradiation position of the proton beam is measured with the position monitor 27A therewith, thereby obtaining an irradiation time recording unit 64 for recording the time as proton beam irradiation data as illustrated in FIG. 8.

In the proton beam therapy system 1A of the modification corresponding to the gate irradiation method, in order to calculate the interaction effect, in an information integration unit 46A of a dose calculation system 45A, a process content of the method for generating the actual spot data is different from that of the information integration unit 46 of the proton beam therapy system 1 described above.

In the modification, the information integration unit 46A of the dose calculation system 45A synchronizes the irradiation time and the tracking time, thereby calculating the position of the marker 32 being irradiated with the particle beam and the irradiation amount of the particle beam and the irradiation position then, and generating the actual spot data in consideration of an influence of the movement of the target 31A as a position error of the spot.

Hereinafter, a method for generating the actual spot data in the modification in which the influence of the movement of the target 31A is considered as the position error of the spot will be described with reference to FIG. 9. Each step described hereinafter is executed instead of step S403 shown in FIG. 5, and since other processes are the same as those in steps S401 to S408 shown in FIG. 5, details thereof will be omitted.

First, when receiving an acquisition instruction signal of log data, the dose calculation control system 44A reads the marker position data stored in the second storage system 63 connected to the moving body tracking control system 65, and outputs the read maker position data to the first storage system 42 together with the proton beam irradiation data stored in the first storage system 42 connected to the proton beam irradiation control system 41A (step S801).

Continuously, the information integration unit 46A of the dose calculation system 45A synchronizes the marker position data acquired from the second storage system 63 with the proton beam irradiation data acquired from the first storage system 42 (step S802).

Specifically, since the time recorded in each data is based upon the timing when the X-ray imaging start button is pressed, the time in each data can be synchronized with each other. Therefore, based upon the recorded time, the position of the marker 32 at the moment when each spot is irradiated is obtained. The marker position data is recorded every 33 ms when imaging is performed by an X-ray at 30 Hz. The position of the marker 32 at the moment when each spot is irradiated can be set to marker position data closest to the time, or may be interpolated from the two marker position data before and after the time.

Next, the information integration unit 46A of the dose calculation system 45A calculates the irradiation position in consideration of the error caused by the movement of the target 31A. Specifically, the information integration unit 46A of the dose calculation system 45A generates the actual spot data in consideration of the influence of the movement of the target 31A as the position error of the spot (step S803).

Here, first, the information integration unit 46A projects the position of the target 31A at the time of the spot irradiation calculated in the previous step S802 onto a plane including an isocenter perpendicular to the beam axis of the proton beam different depending on the angle of the gantry, and obtains coordinates in an X direction and a Y direction in the plane.

Here, the X direction and the Y direction coincide with scanning directions of the two pairs of scanning magnets 26A and 26B, respectively. For example, in the case of the X direction as an example, when the target 31A moves by L in the X direction, the dose distribution is calculated on the assumption that the position of the proton beam moves by −L in the X direction. Here, since an influence of the non-rigid movement of the target 31A in the irradiation target 31 is small in the case of the gate irradiation, the influence is regarded as non-existence such that the influence is ignored.

The movement of the target 31A is obtained as described above, thereby making it possible to calculate the dose distribution in consideration of the movement of the target 31A by using one CT image.

As described above, the spatial position irradiated by the proton beam is recorded as the proton beam irradiation data for each spot. Therefore, the information integration unit 46A generates the actual spot data by, when setting an X coordinate of the spot recorded in the proton beam irradiation data as Xs, setting an X coordinate of the spot as Xs-L. The same process is repeatedly performed in the Y direction. The energy is calculated by using a setting value (a value of the planned spot data) of the energy of the proton beam stored in the first storage system 42. The irradiation amount of the actual spot data is defined as a value recorded in the proton beam irradiation data.

The configuration and operation of the proton beam therapy system 1A are not limited to the above-described form.

For example, in the embodiment, it is assumed that the actual dose distribution during irradiation is calculated and evaluated by using only the X-ray CT image for planning imaged prior to a series of irradiation. The dose distribution can be calculated and evaluated by appropriately using an X-ray cone beam CT image (CBCT image) and the X-ray CT image imaged in the middle of the proton beam irradiation for treatment.

According to the configuration of the proton beam therapy system 1A in the above-described modification, the X-ray CBCT image can be obtained by imaging the X-ray image captured by using two sets of X-ray imaging systems while rotating the gantry.

Since such imaging can be performed immediately before or after irradiation, the CT image closest to the state of target 31A at the time of irradiation can be obtained.

Here, in order to calculate the dose distribution, a pixel value referred to as a CT value of the CT image is important because the pixel value is related to composition of a substance. It is known that accuracy of the CT value of the CBCT image is lower than that of a normal CT image due to limitation of a configuration thereof.

Therefore, the CT image generated by causing the X-ray CT image for planning to match the CBCT image and by performing deformation referred to as non-rigid registration is used for calculating the actual dose distribution during irradiation, such that a more accurate actual dose distribution can be calculated and proposed to the medical staff such as a doctor or the like.

While the modification describes a case in which the tracking time recording unit 66 is provided in the moving body tracking control system 65 and the irradiation time recording unit 64 is provided in the proton beam irradiation control system 41A, each of these time recording units may be provided in the dose calculation control system 44A, in another system, and independently.

The irradiation method may be performed with tracking irradiation that tracks the irradiation position based upon the position of the marker 32 or the like instead of the gate irradiation described above. For example, in X-ray tracking irradiation, a direction of a distribution-forming X-ray generator is changed according to the movement of the target 31A, and an irradiation position of the X-ray is changed according to the movement of the target 31A. Even in the case of the particle beam, the tracking irradiation can be performed by adjusting the excitation amount of the scanning magnets 26A and 26B according to the position of the target 31A.

While the modification describes a case in which the tracking target is defined as the marker 32 and the position of the marker 32 is used as the position data, the tracking target can be defined as the target 31A itself, and the position of the target 31A can be used as the position data.

The tracking target is defined as any target that moves in conjunction with the target 31A other than the target 31A, for example, a high-density region such as a bone or the like such as a rib or the like in the irradiation target 31 is defined as the tracking target, and such positions can be used as the position data.

The proton beam therapy system 1A of the modification also obtain the same effect as that of the proton beam therapy system 1 described above.

The proton beam therapy system 1A of the modification further includes: the irradiation time recording unit 64 configured to record the irradiation time at which the particle beam is emitted; the tracking target position measurement unit configured to measure the position of the marker 32 being irradiated with the particle beam; the tracking time recording unit 66 configured to record the tracking time when the position of the market 32 is measured; and the moving body tracking control system 65 that determines whether the position of the target 31A is within the predetermined range based upon the position of the market 32 measured by the tracking target position measurement unit, and that outputs a signal for permitting the extraction of the particle beam to the proton beam irradiation control system 41A when determining that the position of the target 31A is within the range. The dose calculation system 45A calculates the position of the marker 32 being irradiated with the particle beam, and the irradiation amount and irradiation position of the particle beam then by synchronizing the irradiation time and the tracking time, and the proton beam irradiation control system 41A controls the particle beam based upon the signal generated by the moving body tracking control system 65, such that the interaction effect can also be reflected in the actual dose distribution to be obtained or the like, and a more accurate actual dose distribution can be calculated. Accordingly, it is possible to support the medical staff to more quickly and appropriately make the intervention determination for treatment such as the discontinuation of irradiation or the like during irradiation. The accuracy of irradiating the target 31A with the particle beam can be improved.

The dose calculation system 45A uses the X-ray CBCT image imaged by the tracking target position measurement unit before and after the irradiation of the particle beam, or the planned CT image deformed according to the X-ray CT image as the X-ray CT image for specifying the position of target 31A used when calculating the actual dose distribution, thereby making it possible to calculate more accurate actual dose distribution during irradiation, and to allow the medical staff to more appropriately make the intervention determination for treatment such as the discontinuation of irradiation or the like.

<Others>

The present invention is not limited to the above-described embodiments, but can be modified and applied in various ways. The above-described embodiments are described in detail in order to describe the present invention in an easy-to-understand manner, and are not necessarily limited to those including all the described configurations.

For example, while the above-described embodiments describe a case of using a discrete spot scanning method in which the beam extraction is stopped while the irradiation position of the particle beam is moved from one spot to the next spot, and the beam extraction is restarted after the movement is completed, the present invention can use a raster scanning method, line scanning, or the like in which radiation is continuously performed without the interruption of beam extraction while the same slice is scanned.

While the synchrotron 11 is described as an example of an accelerator that accelerates the proton beam, accelerators such as a cyclotron, a synchrocyclotron, or the like can be used as the accelerator.

While the treatment system including one accelerator and one irradiation system is described, a particle therapy system in which a plurality of irradiation systems are provided for one accelerator can be used.

While a case of using the beam transport system 20 is described, the particle beam can be directly transported from the accelerator to the irradiation nozzle 25.

REFERENCE SIGNS LIST 1, 1A: proton beam therapy system
25: irradiation nozzle (particle irradiation system)
27A: position monitor (irradiation position measurement instrument)
27B: dose monitor (irradiation amount measurement instrument
31: irradiation target
31A: target
32: marker (tracking target)
41, 41A: proton beam irradiation control system (irradiation control system)
41b: irradiation sequence division unit (irradiation sequence division system)
42: first storage system
43: first console
44, 44A: dose calculation control system
44a: calculation interval setting unit
45, 45A: dose calculation system
46, 46A: information integration unit
47: dose calculation unit
48: second console (display system)
48a: setting screen
48b: selection region
49: communication system
50: data server
55, 55A: dose distribution evaluation system during irradiation
61A, 61B: X-ray generator for imaging (tracking target position measurement unit)
62A, 62B: X-ray measurement instrument (tracking target position measurement unit)

63: second storage system
64: irradiation time recording unit
65: moving body tracking control system
66: tracking time recording unit

The invention claimed is:

1. A particle therapy system, comprising:
a particle irradiation system for irradiating a target with a particle beam;
an irradiation control system that is configured to control the particle irradiation system;
an irradiation amount measurement instrument that is configured to measure an irradiation amount of the particle beam emitted to the target;
an irradiation position measurement instrument that is configured to measure a position of the particle beam emitted to the target;
a dose calculation system that is configured to calculate an actual dose distribution emitted to the target by using measurement data of the irradiation amount measurement instrument and the irradiation position measurement instrument;
a display system that is configured to display an obtained dose distribution; and
a dose calculation control system that is configured to select calculation intervals for calculating the actual dose distribution and controls a calculation state of the actual dose distribution,
wherein the dose calculation system is configured to store a plurality of the calculation intervals, and at least one of the plurality of the calculation intervals is selected via the dose calculation control system before irradiating the target with the particle beam,
wherein the dose calculation system is configured to calculate, during the irradiation, the actual dose distribution according to the calculation interval selected among the plurality of the calculation intervals,
wherein the plurality of calculation intervals includes at least one of an energy change of changing the particle beam from a first energy to a second energy and an irradiation angle change from a first angle to a second angle,
wherein the dose calculation system:
obtains a previously stored planned dose distribution,
calculates a differential dose distribution between the planned dose distribution and the actual dose distribution at the selected calculation interval, and
calculates an estimated dose distribution by integrating the differential dose distribution for each selected calculation interval with respect to the planned dose distribution, and
calculates a dose evaluation index from the estimated dose distribution,
wherein the display system is configured to display on a screen at least one of the estimated dose distribution and the dose evaluation index.

2. The particle therapy system according to claim 1, further comprising:
an irradiation time recording unit configured to record irradiation time at which the particle beam is emitted;
a tracking target position measurement unit configured to measure a position of a tracking target being irradiated with the particle beam;
a tracking time recording unit configured to record tracking time when the position of the tracking target is measured; and
a moving body tracking control system that is configured to determine whether a position of the target is within a predetermined range based upon the position of the tracking target measured by the tracking target position measurement unit, and that is configured to output a signal for permitting extraction of the particle beam to the irradiation control system when determining that the position of the target is within the range,
wherein the dose calculation system is configured to calculate the position of the tracking target being irradiated with the particle beam, and the irradiation amount and irradiation position of the particle beam then by synchronizing the irradiation time and the tracking time, and
wherein the irradiation control system is configured to control the particle beam based upon the signal generated by the moving body tracking control system.

3. The particle therapy system according to claim 2,
wherein the dose calculation system is configured to use, as an X-ray CT image for specifying the position of the target used when calculating the actual dose distribution, an X-ray CBCT image imaged by the tracking target position measurement unit before and after irradiation of the particle beam or a planned CT image deformed according to the X-ray CT image.

4. The particle therapy system according to claim 1,
wherein the dose calculation system further is configured to display a dose evaluation index calculated from the estimated actual dose distribution on the display system.

5. The particle therapy system according to claim 4,
wherein the dose calculation system further is configured to compare the dose evaluation index and a planned dose evaluation index calculated from the planned dose distribution, and is configured to display a comparison result on the display.

6. The particle therapy system according to claim 1,
wherein the dose calculation system further is configured to compare the estimated dose distribution and the planned dose distribution, and is configured to display a comparison result on the display.

7. The particle therapy system according to claim 1, further comprising:
an irradiation sequence division system that is configured to divide an irradiation sequence into a plurality of sequences of repaint units.

8. The particle therapy system according to claim 1,
wherein the dose calculation system can select a mode in which irradiation of the particle beam is stopped until calculation of the actual dose distribution is completed, and a mode in which the irradiation of the particle beam is continuously performed even though the calculation of the actual dose distribution is not completed in cooperation with the irradiation control system.

9. The particle therapy system according to claim 1,
wherein if the selected calculation interval is the energy change, the actual dose distribution is calculated after irradiation at the first energy and after irradiation of the second energy.

10. The particle therapy system according to claim 1,
wherein if the selected calculation interval is the irradiation angle change, the actual dose distribution is calculated after irradiation at the first angle and after irradiation at the second angle.

11. A dose distribution evaluation system that is configured to calculate a dose distribution of a particle beam emitted to a target during irradiation, the system comprising:
a dose calculation system that is configured to calculate an actual dose distribution emitted to the target by using measurement data of an irradiation amount measurement instrument that is configured to measure an irradiation amount of the particle beam emitted to the target and an irradiation position measurement instrument that is configured to measure a position of the particle beam emitted to the target;
a display system that is configured to display the obtained dose distribution; and
a dose calculation control system that is configured to select calculation intervals for calculating the actual dose distribution, and is configured to control a calculation state of the actual dose distribution,
wherein the dose calculation system is configured to store a plurality of the calculation intervals, and at least one of the plurality of the calculation intervals is selected via the dose calculation control system before irradiating the target with the particle beam,
wherein the dose calculation system is configured to calculate, during the irradiation, the actual dose distribution according to the calculation interval selected among the plurality of the calculation intervals,
wherein the plurality of calculation intervals includes at least an energy change of changing the particle beam from a first energy to a second energy and an irradiation angle change from a first angle to a second angle,
wherein the dose calculation system:
obtains a previously stored planned dose distribution,
calculates a differential dose distribution between the planned dose distribution and the actual dose distribution at the selected calculation interval, and
calculates an estimated dose distribution by integrating the differential dose distribution for each selected calculation interval with respect to the planned dose distribution,
calculates a dose evaluation index from the estimated dose distribution, and
wherein the display system is configured to display on a screen at least one of the estimated dose distribution and the dose evaluation index.

12. A method for operating a particle therapy system including a particle irradiation system for irradiating a target with a particle beam, an irradiation control system that controls the particle irradiation system, an irradiation amount measurement instrument that measures an irradiation amount of the particle beam emitted to the target, and an irradiation position measurement instrument that measures a position of the particle beam emitted to the target, the method comprising:
calculating, by a dose calculation system, an actual dose distribution emitted to the target by using measurement data of the irradiation amount measurement instrument and the irradiation position measurement instrument;
displaying, by a display system, the obtained actual dose distribution;
selecting, by a dose calculation control system, calculation intervals for calculating the actual dose distribution, and controlling, by the dose calculation control system, a calculation state of the actual dose distribution;
storing, by the dose calculation system, the calculation intervals, and at least one of the plurality of the calculation intervals is selected via the dose calculation control system before irradiating the target with the particle beam;
calculating, during the irradiation, the actual dose distribution according to the calculation interval selected among the plurality of calculation intervals,
wherein the plurality of calculation intervals includes at least an energy change of changing the particle beam from a first energy to a second energy and an irradiation angle change from a first angle to a second angle,
wherein the dose calculation system:
obtains a previously stored planned dose distribution,
calculates a differential dose distribution between the planned dose distribution and the actual dose distribution at the selected calculation interval, and
calculates an estimated dose distribution by integrating the differential dose distribution for each selected calculation interval with respect to the planned dose distribution, and
calculates a dose evaluation index from the estimated dose distribution, and
wherein the display system displays on a screen at least one of the estimated dose distribution and the dose evaluation index.

13. The method for operating the particle therapy system according to claim 12, further comprising:
recording, by an irradiation time recording unit, irradiation time at which the particle beam is emitted;
measuring, by a tracking target position measurement unit, a position of a tracking target being irradiated with the particle beam;
recording, by a tracking time recording unit, tracking time when the position of the tracking target is measured;
determining, by a moving body tracking control system, whether a position of the target is within a predetermined range based upon the position of the tracking target measured by the tracking target position measurement unit, and outputting, by the moving body tracking control system, a signal for permitting extraction of the particle beam to the irradiation control system when it is determined that the position of the target is within the range;
calculating, by the dose calculation system, the position of the tracking target being irradiated with the particle beam, and the irradiation amount and irradiation position of the particle beam then by synchronizing the irradiation time and the tracking time; and
controlling, by the irradiation control system, the particle beam based upon the signal generated by the moving body tracking control system.

* * * * *